(12) United States Patent   (10) Patent No.: US 8,201,440 B2
Brougher                        (45) Date of Patent:     Jun. 19, 2012

(54) LARGE DIAMETER HARDNESS TESTER

(75) Inventor: Wade P Brougher, Houston, TX (US)

(73) Assignee: Blake Brougher, Houston, TX (US)

( * ) Notice: Subject to any disclaimer, the term of this patent is extended or adjusted under 35 U.S.C. 154(b) by 407 days.

(21) Appl. No.: 12/623,808

(22) Filed: Nov. 23, 2009

(65) Prior Publication Data

US 2010/0126257 A1    May 27, 2010

Related U.S. Application Data

(60) Provisional application No. 61/116,884, filed on Nov. 21, 2008.

(51) Int. Cl.
*G01N 3/48* (2006.01)
*G01N 3/00* (2006.01)
(52) U.S. Cl. ............................................. 73/81; 73/78
(58) Field of Classification Search ............... 73/81, 78
See application file for complete search history.

(56) References Cited

U.S. PATENT DOCUMENTS

| | | | | |
|---|---|---|---|---|
| 3,754,436 | A | * | 8/1973 | Saxton .............................. 73/81 |
| 5,438,863 | A | * | 8/1995 | Johnson ........................ 73/54.02 |
| H1554 | H | * | 7/1996 | Horton .............................. 73/82 |
| 6,332,364 | B1 | * | 12/2001 | Buschmann et al. ........... 73/788 |

* cited by examiner

*Primary Examiner* — Harshad Patel
*Assistant Examiner* — Jamel Williams
(74) *Attorney, Agent, or Firm* — Bracewell & Giuliani LLP

(57) ABSTRACT

An apparatus for testing the hardness of a metal work piece having a bore, the apparatus having a horizontal support beam with an axis. A hardness tester is connected to a medial portion of the horizontal support beam. A pair of vertical guide beams are positioned on opposite sides of the hardness tester and are adapted to capture a work piece therebetween. Each vertical guide beam is connected on an upper end to the horizontal support beam at a transverse angle to the axis. At least one of the vertical guide beams being is capable of movement along the axis. A horizontal support rod is releasably connected to and extends between the lower ends of the vertical guide beams and is adapted to extend through the bore of the work piece to enable to the work piece to be lifted by the apparatus.

19 Claims, 2 Drawing Sheets

LARGE DIAMETER HARDNESS TESTER

This application claims priority to provisional application 61/116,884, filed Nov. 21, 2008.

FIELD OF THE INVENTION

This invention is an apparatus for use in testing the hardness of a metal work piece with a bore and a large outer diameter.

BACKGROUND OF THE INVENTION

Hardness testers, for example, Brinell hardness testers, are used to measure the hardness of materials. Hardness is the property of a material that enables it to resist plastic deformation, usually be penetration. Standard Brinell hardness testers are available commercially, however, are often limited in application to test or work pieces of a particular size. For example, a standard Brinell hardness tester may be limited to test or work pieces not exceeding 20 inches. If a test or work piece exceeding the size limitation it tested, accuracy of the Brinell hardness may be negatively affected, resulting in incorrect readings. An apparatus and method is desired that allows accurate measurement of Brinell hardness for large test or work pieces.

SUMMARY OF THE INVENTION

An apparatus for testing the hardness of a metal work piece having a bore has a horizontal support beam with an axis. A hardness tester is connected to a medial portion of the horizontal support beam. A pair of vertical guide beams are positioned on opposite sides of the hardness tester and are adapted to capture a work piece therebetween. Each vertical guide beam is connected on an upper end to the horizontal support beam at a transverse angle to the axis. At least one of the guide beams is capable of movement along the axis of the horizontal support beam. A horizontal support rod is releasably connected to and extends between the lower ends of the vertical guide beams and is adapted to extend through the bore of the work piece to enable to the work piece to be lifted by the apparatus.

The testing apparatus is lifted to a desired height, such that the hardness tester is positioned above the outer surface of the work piece. At least one of the vertical guide beams is positioned along the axis of the horizontal support beam so that the vertical guide beams capture the work piece between them. The support rod is inserted into and through lower ends of the vertical guide beams and the bore of the work piece, thereby connecting the lifting apparatus to the work piece. The testing apparatus is lifted until the support rod is in contact with the inner diameter of the work piece. The probe of the hardness tester is lowered into contact with an outer surface of the work piece and the hardness of the work piece is tested.

DETAILED DESCRIPTION OF THE INVENTION

Figure 1:
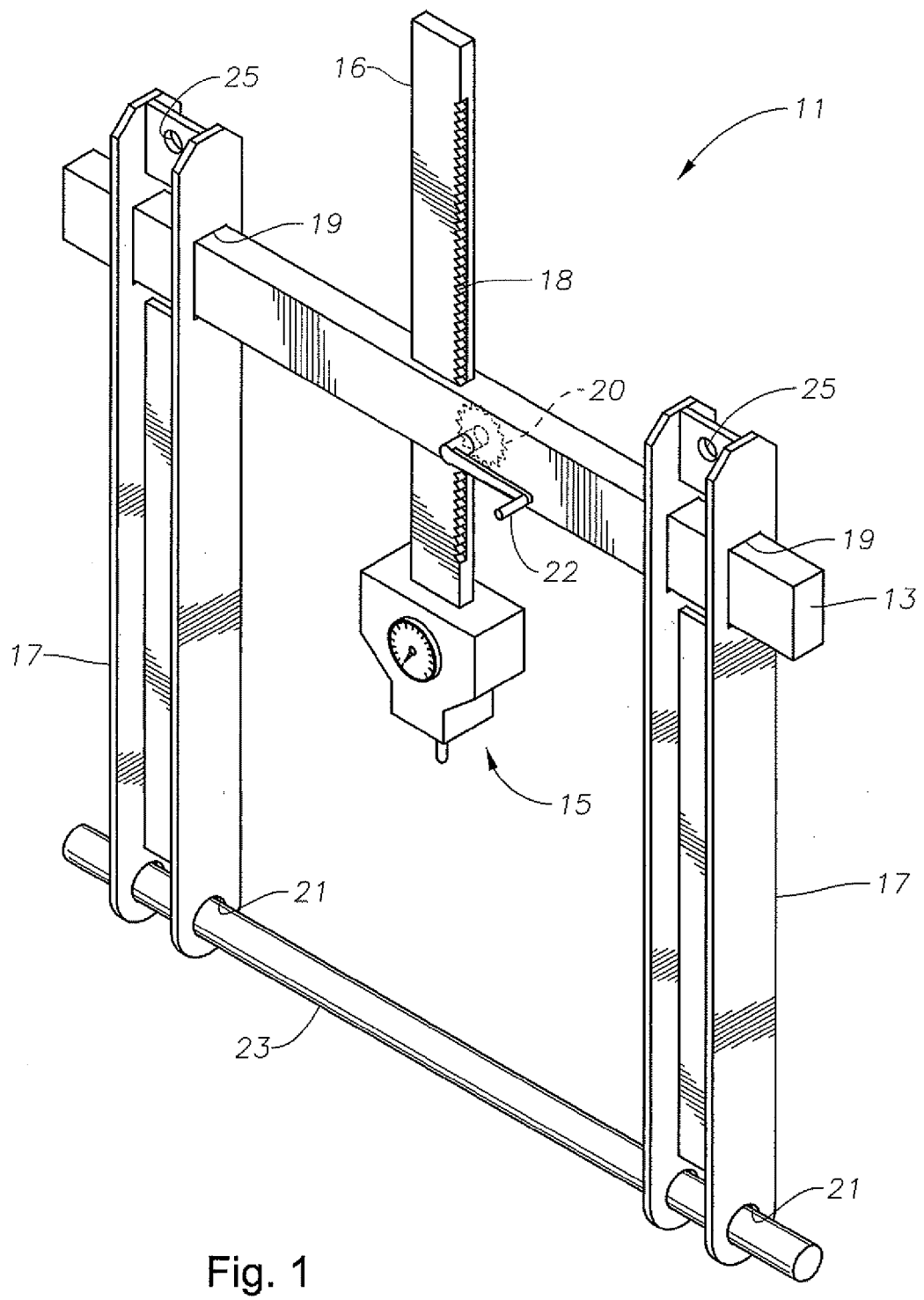
FIG. 1 is a perspective view of a large diameter hardness tester as comprised by the present invention.

FIG. 1 illustrates a large diameter hardness tester assembly 11 as comprised by the present invention. Hardness tester assembly 11 is comprised of a horizontal support beam 13, a standard hardness tester 15, a pair of vertical guide beams 17, and a horizontal support rod 23. The length of support beam 13 may be determined based on the length of the work piece to be tested. A standard hardness tester 15 is mounted near the center of support beam 13 on an elongated vertical support member 16. In this particular embodiment, an elongated support member 16 has a rack of teeth 18 that are engaged by a gear 20 that is connected to support beam 13. A hand crank 22 rotates gear 20 to raise and lower hardness tester 15 relative to horizontal support beam 13. Hardness tester 15 is of a standard variety available commercially with threaded posts and a gear train with a hand crank. Although rack 18, gear 20, and crank 22 are used to adjust the position of hardness tester 15, other devices and methods may be used in alternate embodiments.

To the left and right of hardness tester 15, two vertical guide beams 17 are connected to support beam 13. Support beam 13 passes through machined holes or apertures 19 on the upper end of each guide beam 17. As a result, vertical beams 17 act like sleeves and are capable of moving along the axis of horizontal beam 13.

Opposite holes 19, each beam 17 also has a hole or aperture 21 on its lower end through which a support rod 23 is capable of passing through. Similar to the connection between support beam 13 and guide beams 17, vertical beams 17 are capable of moving along the axis of the support rod 23. Likewise, support rod 23 is capable of movement relative to guide beams 17. The length of support road 23 may be equal to that of support beam 13, which is determined by the length of the work piece to be tested. Holes or apertures 25 are placed in the upper ends of each guide beam 17, above machined holes 19. Holes 25 are capable of receiving a chain, or other fastener device.

Figure 2:
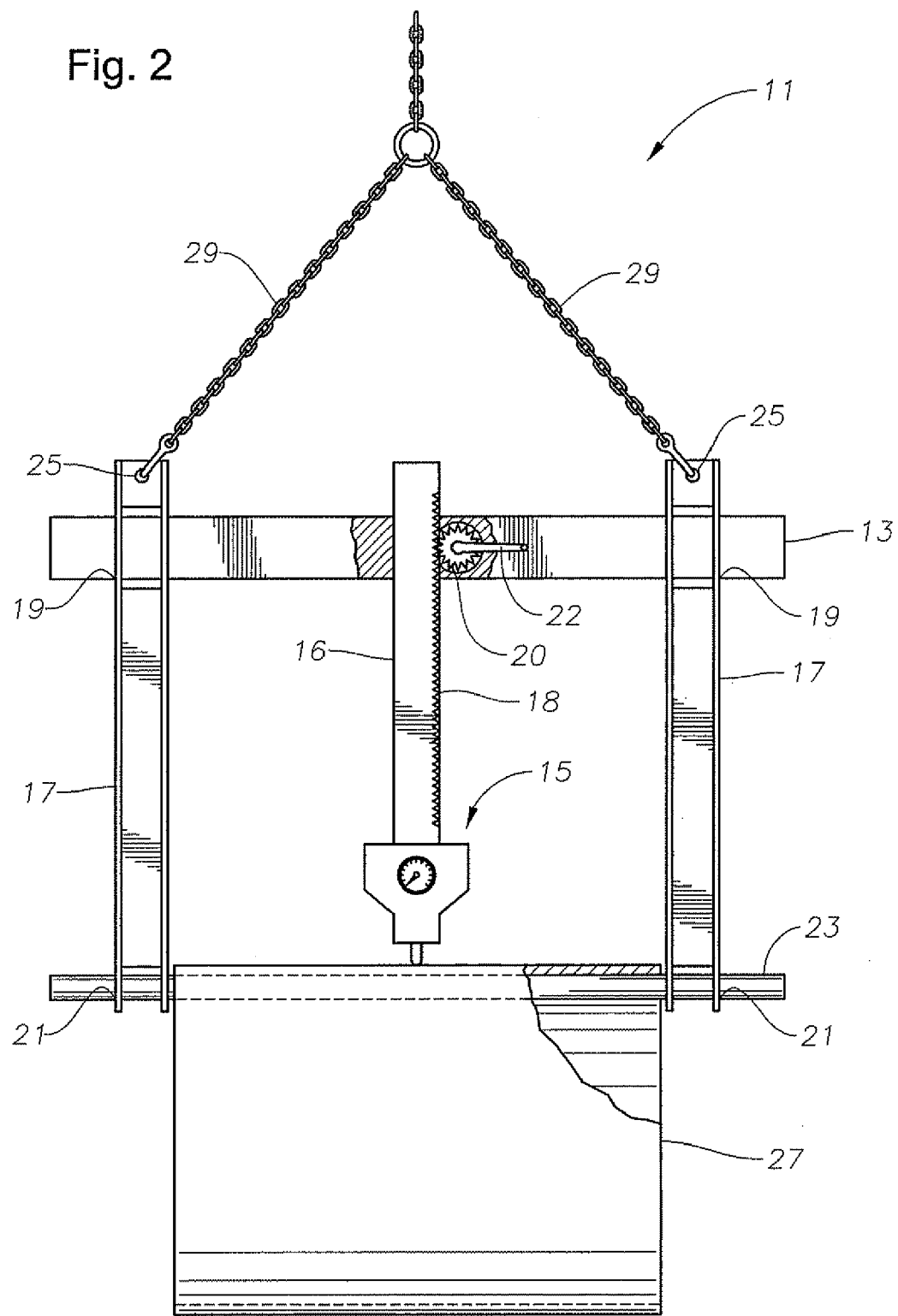
FIG. 2 is a side view of the large diameter hardness tester of FIG. 1 while testing a large diameter work piece.

As illustrated by FIGS. 1 and 2, in operation, a work piece 27 of a certain length with a large outer diameter is to be tested in hardness testing assembly 11. Chains 29 are connected to holes 25 on the upper ends of each vertical guide beam 17. Support rod 23 is removed from the assembly through holes 21. A lifting device simultaneously lifts chains 29 or other fastener devices connected to holes 25. Horizontal beam 13 and vertical guide beams 17 are lifted to a desired height, such that hardness tester 15 is positioned above the outer surface of work piece 27.

Vertical guide beams 17 are then positioned so that they capture work piece 27 between them. It is not necessary that guide beams 17 abut the ends of work piece 27. Work piece 27 should be positioned such that vertical support beams 17 are located at opposite ends of a length of work piece 27. Vertical guide beams 17 may be adjusted along the axis of beam 13 by sliding them in one direction or another. Assembly 11 may need to be raised or lowered so that holes 21 on the lower ends of each vertical support beam 17 are aligned with the interior or bore of work piece 27. Support rod 23 is then inserted through hole 21 on one support beam. Support rod 23 is extended through the bore of work piece 27 and through hole 21 on the opposite support beam 17.

In order to test the hardness of work piece 27, once assembly 11 has been positioned as described above, a lifting device lifts the entire assembly 11 until support rod 23 is in contact with the inner diameter of work piece 27. The assembly 11 and work piece 27 are then raised until work piece 27 is no longer on the ground. Once work piece 27 is off the ground, standard hardness tester 15 is lowered to the proper position by hand crank 22, and the hardness of work piece 27 is tested. Tester 15 has a probe that makes an indentation in the surface of metal work piece 27 when a predetermined force is applied. The force is reacted from support member 16 into horizontal support beam 13. Tester 15 is then moved upward from work piece 27, and the operator measures the diameter of the indentation. The diameter is proportional to a Brinell hardness of work piece 27.

The invention has several advantages. For example, the testing apparatus and method allows the hardness of large test or work pieces to be accurately tested.

While the invention has been shown or described in only some of its forms, it should be apparent to those skilled in the art that it is not so limited, but is susceptible to various changes without departing from the scope of the invention.

The invention claimed is:

1. An apparatus for testing the hardness of a metal work piece having a bore, the apparatus comprising:
    a horizontal support beam having an axis;
    a hardness tester connected to a medial portion of the horizontal support beam;
    a pair of vertical guide beams positioned on opposite sides of the hardness tester adapted to capture a work piece therebetween, each beam connected on an upper end to the horizontal support beam at a transverse angle to the axis, at least one of the guide beams being capable of movement along the axis; and
    a horizontal support rod releasably connected to and extending between lower ends of the vertical guide beams and adapted to extend through the bore of the work piece to enable the work piece to be lifted by the apparatus.

2. The apparatus of claim 1, wherein the hardness tester is capable of movement perpendicular to the axis.

3. The apparatus of claim 1, wherein each vertical guide beam is connected to the horizontal support beam at a substantially perpendicular angle to the axis.

4. The apparatus of claim 1, wherein both of the guide beams are capable of movement along the axis.

5. The apparatus of claim 1, wherein the hardness tester further comprises:
    an elongated support member having a rack of teeth;
    a gear, mechanically engaged with the rack of teeth; and
    a hand crank for rotating the gear, thereby moving the hardness tester relative to the horizontal support beam.

6. The apparatus of claim 1, further comprising:
    a lifting device connected to the upper ends of the vertical guide beams for lifting the apparatus to a desired height.

7. The apparatus of claim 1, wherein each vertical guide beam has an aperture located in and extending through the upper end; and
    wherein the horizontal support beam extends through the apertures in the upper ends of the vertical guide beams, thereby allowing the vertical guide beams to move along the axis.

8. The apparatus of claim 1, wherein each vertical guide beam has an aperture located in and extending through the lower end; and
    wherein the horizontal support rod extends through the apertures in the lower ends of the vertical guide beams.

9. The apparatus of claim 1, further comprising:
    an aperture located in and extending through the upper end of each vertical guide beam; and
    a lifting device connected to each aperture in the upper end of the vertical guide beams for lifting the apparatus to a desired height.

10. An apparatus for testing the hardness of a metal work piece having a bore, the apparatus comprising:
    a horizontal support beam having an axis;
    a hardness tester connected to an elongated support member mounted to a medial portion of the horizontal support beam;
    a drive mechanism for raising and lowering the elongated support member;
    a pair of vertical guide beams positioned on opposite sides of the hardness tester adapted to capture a work piece therebetween, each beam connected on an upper end to the horizontal support beam at a transverse angle to the axis, the guide beams being capable of movement along the axis;
    a horizontal support rod releasably connected to and extending between lower ends of the vertical guide beams and adapted to extend through the bore of the work piece to enable the work piece to be lifted by the apparatus; and
    a lifting device connected to the upper ends of the vertical guide beams for lifting the apparatus to a desired height.

11. The apparatus of claim 10, wherein the hardness tester is capable of movement perpendicular to the axis.

12. The apparatus of claim 10, wherein each vertical guide beam is connected to the horizontal support beam at a substantially perpendicular angle to the axis.

13. The apparatus of claim 10, wherein the elongated support member further comprises:
    a rack of teeth extending along its length; and wherein
    the drive mechanism comprises a gear, mechanically engaged with the rack of teeth, and a hand crank for rotating the gear, thereby moving the hardness tester relative to the horizontal support beam.

14. The apparatus of claim 10, wherein each vertical guide beam has an aperture located in and extending through the upper end; and
    wherein the horizontal support beam extends through the apertures in the upper ends of the vertical guide members, thereby allowing the vertical guide beams to move along the axis.

15. The apparatus of claim 14, wherein each vertical guide beam has an aperture located in and extending through the lower end; and
    wherein the horizontal support rod extends through the apertures in the lower ends of the vertical guide members.

16. The apparatus of claim 10, further comprising:
    an aperture located in and extending through the upper end of each vertical guide beam; and
    wherein the lifting device is connected to each aperture in the upper end of each vertical guide member for lifting the apparatus to a desired height.

17. A method for testing the hardness of a metal work piece having a bore, the method comprising:
    (a) providing a testing apparatus comprising a horizontal support beam having an axis, a hardness tester connected to a medial portion of the horizontal support beam, a pair of vertical guide beams positioned on opposite sides of the hardness tester, each beam connected on a first end to the horizontal support beam at a transverse angle to the axis, at least one of the guide beams being capable of movement along the axis;
    (b) lifting the testing apparatus to a desired height, such that hardness tester is positioned above the outer surface of the work piece;
    (c) positioning at least one of the vertical guide beams along the axis of the horizontal support beam so that the vertical guide beams capture the work piece between them;

(d) inserting a support rod into and through lower ends of the vertical guide beams and the bore of the work piece, thereby connecting the lifting apparatus to the work piece;
(e) lifting the testing apparatus until the support rod is in contact with the inner diameter of the work piece; and
(f) lowering a probe of the hardness tester into contact with an outer surface of the work piece and testing the hardness of the work piece.

18. The method of claim 17, wherein step (c) further comprises:

positioning both of the vertical guide beams along the axis of the horizontal support beam so that they capture the work piece between them.

19. The method of claim 17, wherein step (e) further comprises:

lifting the testing apparatus until the work piece is no longer on the ground.

\* \* \* \* \*